(12) United States Patent
Bode et al.

(10) Patent No.: US 9,687,182 B2
(45) Date of Patent: Jun. 27, 2017

(54) MEDICAL SENSOR SYSTEM FOR DETECTING A FEATURE IN A BODY

(75) Inventors: Sven Bode, Berlin (DE); Andreas Bunge, Leipzig (DE); Sarah Biela, Berlin (DE); Hoc Khiem Trieu, Westergellersen (DE)

(73) Assignee: BIOTRONIK SE & Co. KG (DE)

( * ) Notice: Subject to any disclaimer, the term of this patent is extended or adjusted under 35 U.S.C. 154(b) by 1672 days.

(21) Appl. No.: 13/248,095

(22) Filed: Sep. 29, 2011

(65) Prior Publication Data

US 2012/0088994 A1 Apr. 12, 2012

Related U.S. Application Data

(60) Provisional application No. 61/390,621, filed on Oct. 7, 2010.

(51) Int. Cl.

| | |
|---|---|
| *A61B 5/00* | (2006.01) |
| *A61B 5/1473* | (2006.01) |
| *A61B 5/145* | (2006.01) |
| *B01D 69/14* | (2006.01) |
| *B01D 71/06* | (2006.01) |
| *F15C 1/00* | (2006.01) |
| *F16K 99/00* | (2006.01) |

(52) U.S. Cl.
CPC ...... *A61B 5/14735* (2013.01); *A61B 5/14503* (2013.01); *A61B 5/14532* (2013.01); *A61B 5/14535* (2013.01); *A61B 5/14539* (2013.01); *A61B 5/14546* (2013.01); *B01D 69/148* (2013.01); *B01D 71/06* (2013.01); *F15C 1/008* (2013.01); *F16K 99/0001* (2013.01); *A61B 2562/02* (2013.01); *A61B 2562/028* (2013.01); *A61B 2562/04* (2013.01)

(58) Field of Classification Search
CPC .......... A61B 2562/02; A61B 2562/028; A61B 2562/04
See application file for complete search history.

(56) References Cited

U.S. PATENT DOCUMENTS

| | | |
|---|---|---|
| 5,290,240 A | 3/1994 | Horres, Jr. |
| 5,368,571 A | 11/1994 | Horres, Jr. |
| 6,527,762 B1 | 3/2003 | Santini, Jr. et al. |
| (Continued) | | |

FOREIGN PATENT DOCUMENTS

| | | |
|---|---|---|
| WO | WO 01/26708 A1 | 4/2001 |
| WO | WO 02/20877 A1 | 3/2002 |
| WO | WO 2008/154416 A2 | 2/2008 |

OTHER PUBLICATIONS

Albu et al., "Self-organized, free-standing TiO2 nanotube membrane for flow-through photocatalytic applications," Nano Lett. May 2007; 7(5):1286-9 (Epub Apr. 25, 2007).

*Primary Examiner* — Patricia Mallari
*Assistant Examiner* — Karen Toth
(74) *Attorney, Agent, or Firm* — Craig A. Fieschko, Esq.; DeWitt Ross & Stevens S.C.

(57) ABSTRACT

The invention relates to a medical sensor system (10) for detecting a feature (12), such as an analyte, in a human or animal body. The system (10) includes at least one sensor (14; 34) having a reservoir (18) with a cap (16) designed as a controllable organic membrane (20), wherein (for example) application of a voltage of a particular magnitude, or application of a voltage for a particular time, effects a change in the permeability of the membrane (20).

20 Claims, 7 Drawing Sheets

(56) References Cited

U.S. PATENT DOCUMENTS

| | | | |
|---|---|---|---|
| 2001/0029348 A1* | 10/2001 | Willis | A61B 5/14532 604/20 |
| 2004/0006300 A1 | 1/2004 | Willis | |
| 2005/0072689 A1 | 4/2005 | Spohr et al. | |
| 2008/0213133 A1 | 9/2008 | Wallace et al. | |
| 2009/0024114 A1 | 1/2009 | Hood et al. | |
| 2009/0317445 A1 | 12/2009 | Van Bruggen et al. | |
| 2009/0326279 A1* | 12/2009 | Tonkovich | B01F 5/0475 568/487 |
| 2010/0241086 A1* | 9/2010 | Yodfat | A61B 5/14525 604/246 |
| 2012/0029416 A1* | 2/2012 | Parker | A61F 13/02 604/20 |

\* cited by examiner

MEDICAL SENSOR SYSTEM FOR DETECTING A FEATURE IN A BODY

CROSS-REFERENCE TO RELATED APPLICATIONS

This patent application claims the benefit of U.S. Provisional Patent Application No. 61/390,621, filed on Oct. 7, 2010, which is hereby incorporated by reference in its entirety.

FIELD OF THE INVENTION

The invention relates to a medical sensor system for detecting at least one feature in at least one human and/or animal body.

BACKGROUND OF THE INVENTION

In medicine, sensor systems are used wherein at least parts of the systems are inserted or implanted directly in a body of a patient in order to capture actual physiological conditions as precisely and directly as possible.

Publication WO 2008/154416 A2, in combination with U.S. Pat. No. 6,527,762 B1, discloses a sensor that can be implanted in the body, wherein a sensor has a reservoir capped by a thin metal film. By use of a thermal process wherein a voltage is applied, the cap is irreversibly removed to expose the interior of the sensor. The sensor's interior is continually subjected to degradation processes, and moreover, pieces of the metal film can enter the body, which can be harmful.

SUMMARY OF THE INVENTION

The invention seeks to provide a medical sensor system for detecting a feature in a body, and which can be flexibly used, and implemented in a robust manner that is resistant to error. In this context, "sensor" refers to a component that can detect a physical and/or chemical property of a parameter in the sensor's environment, qualitatively and/or quantitatively, preferably as a quantity to be measured. A "sensor system" refers to a system having at least one sensor, and which can include further components, such as further sensors, a housing, electronic components, a power supply, a telemetry unit, a control unit, an anchoring device, and/or any other suitable component. A "feature" refers to a parameter such as a pH value, a charge (e.g. of an ion or a polyelectrolyte), a temperature, a mass, an aggregation state, water content, hematocrit value, and/or a presence or absence and/or a quantity of an analyte or other substance (such as a fat, a salt, an ion, a polyelectrolyte, a sugar, a nucleotide, DNA, RNA, a peptide, a protein, an antibody, an antigen, a drug, a toxin, a hormone, a neurotransmitter, a metabolite, a metabolic product, and/or any other analyte of interest). A "feature" also refers to so-called biomarkers which form a variable component of the human or animal body, such as albumins/globulins, alkaline phosphatase, alpha-1-globulin, alpha-2-globulin, alpha-1-antitrypsin, alpha-1-fetoprotein, alpha-amylases, alpha-hydroxybutyrate-dehydrogenase, ammonia, antithrombin III, bicarbonate, bilirubin, carbohydrate antigen 19-9, carcinoembryonic antigens, chloride, cholesterol, cholinesterase, cobalamin/vitamin B12, coeruloplasmin, C-reactive proteins, cystatin C, D-dimers, iron, erythropoetin, erythrocytes, ferritin, fetuin-A fibrinogen, folic acid/vitamin B9, free tetrajodthyronine (fT4), free trijodthyronine (fT3), gamma-glutamyl transferase, glucose, glutamate dehydrogenase, glutamate oxaloacetate transaminase, glutamate pyruvate transaminase, glycohemoglobin, hematocrit, hemoglobin, haptoglobin, uric acid, urea, HDL cholesterol, homocysteine, immunoglobulin A, immunoglobulin E, immunoglobulin G, immunoglobulin M, INR, calium, calcium, creatinine, creatine kinase, copper, lactate, lactate dehydrogenase, LDL cholesterol, leukocytes, lipase, lipoprotein, magnesium, corpuscular hemoglobins, myoglobin, sodium, NT-proBNP/BNP, phosphate, prostate-specific antigens, reticulocytes, thrombocytes, transferrin, triglycerides, troponin T, or drugs such as muscarinic receptor antagonists, neuromuscular blocking substances, cholesterol esterase inhibitors, adrenoceptor agonists, indirectly acting sympathomimetics, methylxanthine, alpha-adrenoreceptor antagonists, ergot alkaloids, beta-adrenoceptor antagonists, inactivation inhibitors, antisympathonics, 5-HT receptor agonists, histamine receptor agonists, histamine receptor antagonists, analgesics, local anesthetics, sedatives, anticonvulsants, convulsants, muscle relaxants, antiparkinsonians, neuroleptics, antidepressants, lithium, tranquilizers, immunsuppressants, antirheumatics, antiarrhythmics, antibiotics, ACE inhibitors, aldosterone receptor antagonists, diuretics, vasodilatators, positive inotropic substances, antithrombotic/thrombolytic substances, laxatives, antidiarrheal agents, pharmaceuticals for adiposity, uricostatics, uricosurics, antilipemics, antidiabetics, antihypoglycemia, hormones, iodized salts, threostatics, iron, vitamins, trace elements, virostatics, antimycotics, antituberculotics, and substances for tumor chemotherapy. However, any other feature of interest for detection can be detected by the sensor system. The feature preferably relates to a variable component of the animal body and/or human body. A preferred version of the sensor system is used to detect a member of the cystatin family of the cysteine protease inhibitors, particularly to detect cystatin C.

The sensor system includes at least one sensor and at least one cap of a reservoir of the sensor, wherein the cap is designed as a controllable organic membrane. "Reservoir of the sensor" or "sensor reservoir" refers to a space, a chamber, and/or a cavity of the sensor in contact with a detection system of the sensor, and/or on and preferably in which the detection system is disposed. Furthermore, the sensor reservoir encloses a volume that contains or has the feature to be detected. "Cap" refers to a device and/or a component of the sensor reservoir that closes the sensor reservoir in at least one operating state of the sensor system, and/or prevents the sample volume from entering into and/or emerging from the sensor reservoir. The cap is therefore a functional component of the sensor. "Controllable" is intended to mean that the membrane can be switched via at least one signal from at least one selected starting state to a selected end state. The signal is an influence that can act from outside of the sensor system, such as radiation, infrared, visible light, ultrasound, an electrical field, a magnetic field, a protein, a peptide, a polyelectrolyte, a change in a pH value, a change in ion concentration, a temperature change, and/or any other effect suitable for use as a signal. Preferably, a volume of the membrane can be controlled. The term "organic membrane" refers to a separating layer and/or a thin film which includes at least one component based on a carbon compound.

The controllable organic membrane can change its state in response to the triggering signal in a manner such that at least a portion of the membrane is permeable to the analyte, thereby providing the analyte with access to the detection system. Moreover, the controllable organic membrane can be changed, reversibly and steplessly, between an open state and a closed state of the reservoir. "Steplessly" refers to the possibility of adjusting the opening width of the membrane to any width up to a maximum limit "Reversibly" means in a manner than can be reversed. By making it possible to reverse the change, the detection system disposed in the sensor reservoir can be protected against interfering molecules that could attack, degrade, and/or destroy the sensor. Other interfering factors that can impair the proper functioning of the sensor are also minimized in this manner. As a result, a sensor system having a particularly long service life can be provided.

The controllable organic membrane is advantageously closed before an initial use or an initial measurement run of the sensor, thereby effectively protecting the sensor against disturbing influences such as dirt, dust, excessive humidity, dryness, temperature fluctuations, and/or harmful molecules before initial start-up. It is additionally advantageous when the controllable organic membrane can be closed between the individual measurements, thereby ensuring that the components of the sensor system can remain stable.

The controllable organic membrane includes at least one pore, the diameter of which can be changed in a reversible manner, whereby the state of the membrane (and passage of an analyte into the sample volume) can be structurally adapted to allow passage of different molecules and/or analytes. Preferably, at least one of the opening of the pore and the closing of the pore can be controlled. The pore is preferably a nanopore with a maximum diameter of approximately 1 µm. The pores need not have a round shape/contour, and can alternatively or additionally have oval, triangular, square, or other polygonal shapes, star-shapes, or any other desirable shapes. The nanopores make it easy to prevent structures such as cells, large molecules, or molecular aggregates having a greater dimension than the diameter of the nanopores from entering the sample volume from the sensor's environment and interfering with the detection system. The membrane preferably includes a large number of similar pores that are distributed evenly over a surface of the membrane, though an inhomogeneous pore distribution is also possible. Preferably the pore diameter is steplessly adjustable, which enables it to be used with a large number of analytes.

The controllable organic membrane preferably includes at least one material that has a changeable redox (reduction of oxidation) state, enabling the permeability of the membrane to be easily and reliably changed. The redox state can be changed chemically, electrically, and/or via other means.

For simplicity and convenience, it is useful if the controllable organic membrane is electrically controllable, in particular, if the pores (e.g., their size and/or shape) are electrically controllable. In preferred versions of the invention, this occurs by applying a voltage of approximately 2 V at most. When the nanopores are fully open, the volume of the material having the changeable redox state is at its minimum. When a voltage is applied, the volume of the material changes, thereby reducing the pore diameter. The volume increase may usefully be made dependent on the level of the voltage that is applied for a certain period of time, or on the period of time during which a certain voltage is applied; in either case, the voltage need be applied only for a certain period of time, and need not be constantly maintained to effect a change in pore size. The procedure may then be reversed by applying a voltage with reverse polarity, or by use of analogous methods, resulting in a reduction of the volume of the material. The change in volume is dependent on the structural design of the membrane as well as its materials and the stimulus applied to effect the change.

The material that can change its redox state is preferably an electroactive polymer or other material. As an example, if a mixture of polypyrrole (PPy) and dodecylbenzene sulfonic acid (DBS) is used as the electroactive polymer, sodium ions are inserted into the polymer during a voltage-controlled reduction of the polymer. This insertion of sodium ions induces a strongly lateral change in volume of the electroactive polymer, which therefore closes the pores for the analyte. The reversibility of this procedure allows controlled opening and closing of the pores, and therefore controlled and repeatable sensor measurements. The volume of the polymer can be partially changed via the extent of the reduction of the polymer. The redox states of the electroactive polymer are created using different applied voltages, and are retained when the voltage is switched off. As a result, the polymer and pore diameter can be advantageously adjusted for analytes of different sizes.

The detection system includes a receptor layer that brings about a measurable reaction with the feature to be measured, thereby allowing detection of the feature to be measured. The "receptor" can be one or more substances chosen from the classes of peptides, proteins (in particular enzymes), antibodies and their fragments, RNA, DNA, nucleotides, fats, sugars, salts, ions, cyclic macromolecules (such as ionophores, crown ethers, and cryptands), acyclic macromolecules, or other suitable substances. The receptor layer is preferably an antibody layer on a seFET (single electron Field Effect Transistor).

In a preferred version of the invention, the membrane, or the polymer or other material therein which has a changeable redox state, is applied to a nanoporous substance which defines a carrier structure. Preferably, the membrane or the material having the changeable redox state is disposed at least on inner surface of the pores of the nanoporous substance. As a result, the nanopores of the carrier structure can be used as the basic framework of the pore structure. The pore diameter is dependent on the analyte to be detected. Preferably, the pore diameter is selected such that the membrane is permeable to molecules of the analyte, but poses a barrier for larger molecules. If the analyte to be detected is a protein (or an analyte of similar size), the pores might have a maximum diameter of 1 µm, preferably a maximum of 250 nm, furthermore preferably 100 nm, advantageously a maximum of 50 nm, and particularly preferably a maximum of 10 nm. For smaller analytes, the pores can have a maximum diameter of 500 nm, preferably a maximum of 100 nm, furthermore preferably 50 nm, advantageously a maximum of 10 nm, and particularly preferably a maximum of 1 nm. The pores may assume any shape wherein the maximum dimension is sized as described above.

The nanoporous substance preferably contains a metal oxide such as $Al_2O_3$, $In_2O_3$, $MgO$, $ZnO$, $CeO_2$, $CO_3O_4$, and/or the carrier structure at least contains $TiO_2$, though other nanoporous substances could be used. $TiO_2$ allows a particularly lightweight, biocompatible, and bioinert carrier structure. In addition, the nanopore structure may be composed of nanotubes for easy and reproducible synthesis. These highly regular structures can be created relatively easily using an anodizing process. The pore size and layer thickness of this substrate can be easily adjusted by appropriate selection of manufacturing process parameters. The carrier structure thickness of hundreds of micrometers is typically much greater than the diameter of the nanotubes.

The controllable organic membrane preferably has at least one structure on the top side thereof that prevents the adhesion of cells and molecules, to prevent biofouling. As an example, $TiO_2$ nanostructures (as discussed above) can themselves prevent cell adhesion.

Preferably, the complete sensor system is biologically degradable so that it need not be removed from the patient's body once it loses functionality, thereby avoiding the need for invasive explantation procedures. Complete biodegradability also avoids the presence of potentially harmful substances within the patient's body, as may be the case where a non-biocompatible and degradable sensor were used. It is particularly advantageous if the controllable organic membrane is installed on a carrier structure that has high biocompatibility, thereby making it possible to minimize or entirely prevent rejection reactions and inflammatory responses that may affect patient health.

The sensor is preferably designed to determine the feature in a quantitative manner, whereby it may determine the concentration of an analyte in (for example) bodily fluids such as blood, urine, interstitial fluid or lacrimal fluid.

Where the sensor system incorporates two or more sensors for two or more different analytes or other features, space and components savings can be achieved where the sensors are provided at the same region. To illustrate, a first sensor may be designed as a measurement sensor, and a second sensor may be designed as a reference sensor, wherein the two of them form a single piece. (In this context, "single piece" means that the measurement sensor and the reference sensor are defined by the same components, and/or that functionality would be lost if the two were separated.) The sensor reservoir is designed such that it is used in a first mode to perform a reference measurement, and in a second mode which takes place subsequently to the first mode to measure the analyte. To perform the reference measurement, a pore size is selected that is smaller than a diameter of the analyte, thereby preventing the analyte from entering the sample volume. However, molecules or structures that are smaller than the analyte can enter the sample volume. To perform the analyte measurement, the pore size can then be adapted to the size of the analyte, thereby enabling the analyte to enter the sample volume. The measurement signal of the reference measurement can then be subtracted as a background signal (or otherwise removed) from the measurement signal of the analyte measurement to provide a final measured value. Thus, the background signal caused by interfering matter can be easily determined by use of a simple design.

Another version of the sensor system uses first and second sensors at two different regions, thereby making it possible to measure the analyte and perform the reference measurement simultaneously for time savings. The first (measurement) sensor and the second (reference) sensor are preferably disposed in the sensor system such that they are spatially separated. Any type of suitable sensor can be used for the second sensor, though the second sensor preferably includes a reference reservoir which encloses a reference volume, and a (preferably electrically) switchable organic membrane. The two sensors preferably differ in terms of the configuration of their switchable membranes and in terms of the pore sizes implemented therein. The membrane pore size of the first (measurement) sensor allows the analyte to enter the sample volume. A smaller pore size in the second (reference) sensor prevents the analyte from entering the reference volume. The final measured value is obtained by correcting the measurement sensor signal using the reference signal. The different porosities of the measurement sensor and the reference sensor are selected by using different voltage levels and/or by applying the voltage to the sensors' membranes for different durations.

This design has the advantage that drift and aging processes occur simultaneously in both sensors, and where the measurement sensor and the reference sensor are configured with at least substantially the same detection system, it is possible to collect information on the drift (e.g. degradation of the detection system, change in temperature, and other effects) of one sensor with respect to the other. The measured values can be corrected for drift by using a suitable correction term, or can be compensated for by using a suitable electrical, mechanical, chemical/biochemical, or other method. If the drift is so great that these mechanisms are no longer effective, then sensors installed in parallel with the "aged" sensors, which were previously left dormant, might be activated.

The invention also involves a medical sensor array having at least two sensor systems. They can be identically-configured sensor systems that are activated in succession to detect, or determine the concentration of, the same analyte. Alternatively or additionally, the sensor systems can be used simultaneously to measure the analyte and also perform a reference measurement. Another alternative or additional arrangement is to have an array of sensor systems that can detect different analytes and/or their concentrations, either simultaneously or in succession. The use of several sensor systems can allow an effective extension of the limited service life of a single sensor system.

The invention also involves a medical implant which incorporates the medical sensor system, or an array of such systems. The sensor system can be used in any suitable implant, such as an implant for recording physiological parameters, a cardiac pacemaker, a defibrillator, a brain pacemaker, a renal pacemaker, a duodenal pacemaker, a cardiac implant, artificial heart valves, a cochlear implant, a retinal implant, a dental implant, an implant for joint replacement, a vascular prosthesis, a drug delivery system, or particularly advantageously, a stent, such as a coronary stent, a renal artery stent, or a ureteral stent. The sensor system can assist in the function of such implants.

At least a part of the surface of the implant can have hydrophobic or hydrophilic properties, and it can have a cationic, anionic, or metallic character, depending on the implant's usage. Inorganic or organic molecules can be bonded to the surface via physical adsorption or covalent bonds such as polymers, peptides, proteins, aptamers, molecularly imprinted polymers, RNA, DNA, siRNA, and nanoparticles. The surface can have nanostructuring or microstructuring. To provide the surface structure, round, spherical, cylindrical, conical, square, rectangular, or elongated structures, including grooves, tubes, solid cylinders, hollow cylinders, balls, hemispheres, cuboids, and cubes, can be applied to or removed from the surface. A partially bioresorbable or biodegradable surface is also feasible.

It is also possible to attract and immobilize specific structures, e.g. from a bodily fluid, such as certain proteins or cells, on the surface and incite the cells to proliferate. For this purpose, antigens, peptides, proteins, antibodies, aptamers, molecularly imprinted polymers and oligonucleotides (DNA, RNA, PNA, LNA) can be adhered or covalently bound to the surface.

Furthermore, the sensor or the implant can include a telemetry device which is used to transmit the measured values to an external device. The telemetry device can be designed to be bidirectional, thereby making it possible to control the implanted sensor or implant using an external device. The sensor or implant can be a subcomponent of a body-area network, i.e. further sensors, which are likewise interconnected via wireless telemetry and/or which communicate with an external device, can detect physiologically relevant parameters in parallel, such as pressure, pulse, EKG, EEG, biochemical parameters, and/or other desirable parameters.

The invention is also directed to methods for operating medical sensor systems and/or implants such as those described above.

BRIEF DESCRIPTION OF THE DRAWINGS

Exemplary versions of the invention will now be discussed with reference to the figures, which illustrate.

In the figures, functionally equivalent or equivalently acting elements are denoted with the same reference numerals. The figures are schematic illustrations of the invention, and do not depict specific parameters. In addition, the figures only reflect exemplary versions of the invention and are not intended to limit the invention to the versions that are illustrated. So as to avoid unnecessary repetitions, elements in a particular figure that are not described in detail below are provided with a reference to the respective description of the elements in the preceding figures.

DETAILED DESCRIPTION OF EXEMPLARY VERSIONS OF THE INVENTION

Figure 1:
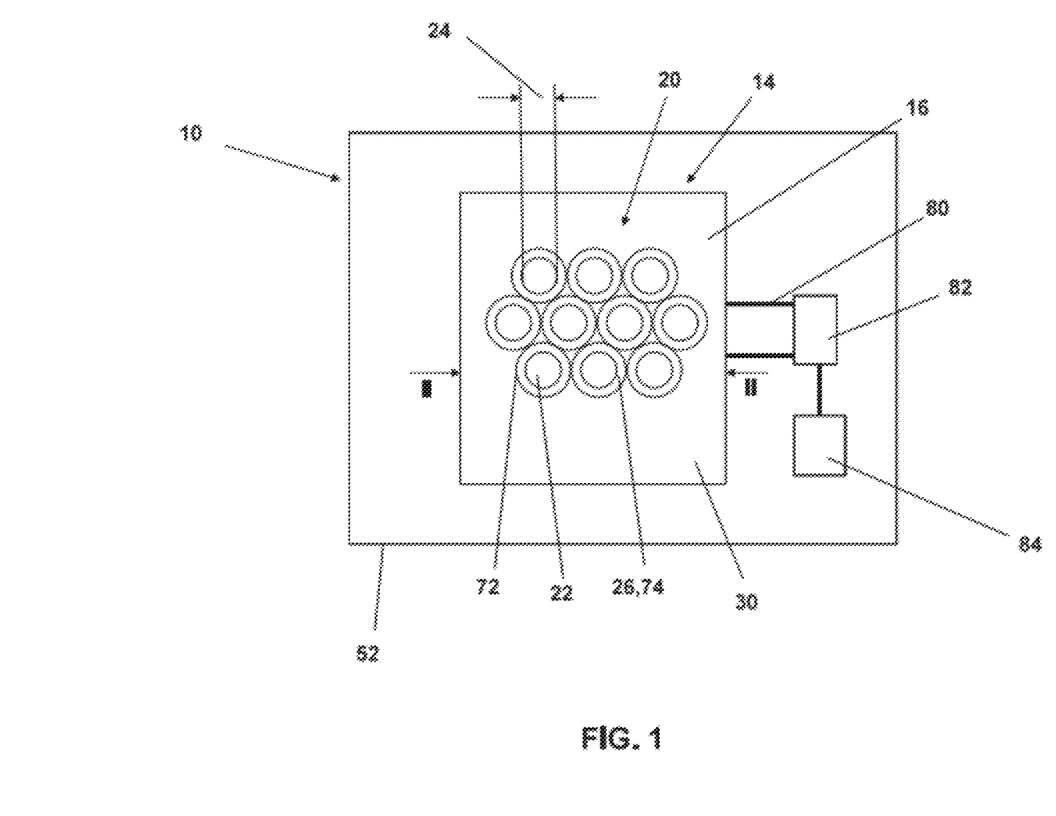
FIG. 1 a schematic view of an exemplary sensor system according to the invention, shown from above, FIG. 2A a schematic view of a cross section along the line II-II through the sensor system depicted in FIG. 1, with the pores closed, FIG. 2B the sensor system depicted in FIG. 2a with the pores in an open state, for purposes of making a reference measurement, FIG. 2C the sensor system depicted in FIG. 2a with the pores in an open state, for purposes of making an analyte measurement, FIG. 3A a detailed depiction of a pore shown in figure FIG. 2a, in the closed state, FIG. 3B a detailed depiction of a pore shown in figure FIG. 2c, in the open state, FIG. 4 the sensor system depicted in FIG. 1, including additional components, FIG. 5A an implant equipped with a sensor system according to FIG. 1, FIG. 5B an alternative implant equipped with a sensor array having four sensor systems according to FIG. 1, FIG. 6 a schematic view of a cross section of an alternative sensor system which includes a measurement sensor and a reference sensor having pores which are open to different extents, FIG. 7A another alternative implant equipped with a sensor system according to FIG. 6, and FIG. 7B a fourth exemplary implant equipped with a sensor array having four sensor systems according to FIG. 6.
Figure 2A:
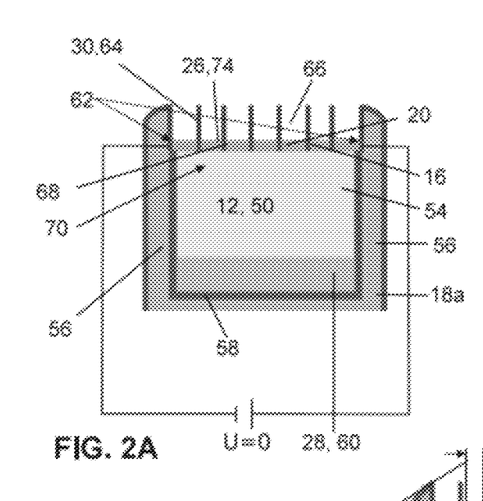
Figure 2B:
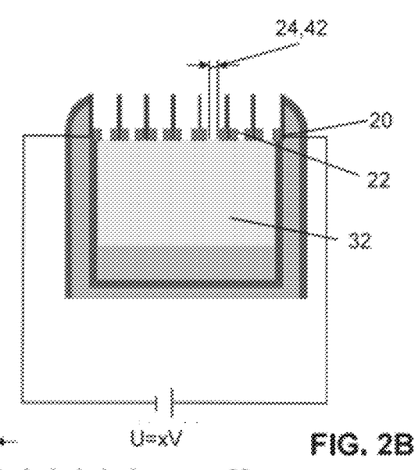
Figure 2C:
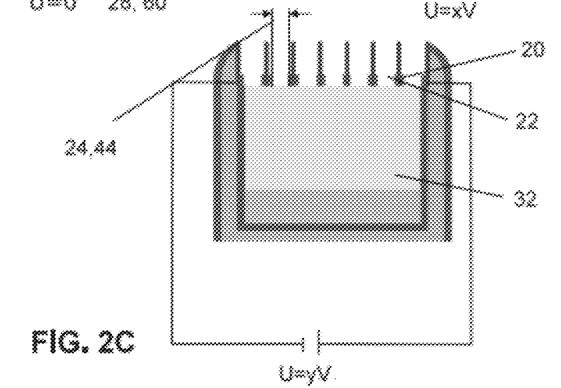

FIG. 1 schematically depicts the top of a medical sensor system 10 for detecting a feature 12 in a human body (the body not being shown here), with FIGS. 2a-2c showing cross-sectional views along the line II-II in FIG. 1 at different times. Feature 12 (FIG. 2a) is an analyte 50 in the form of a protein to be detected. The sensor system 10 includes a sensor 14 which is disposed in a housing 52. As shown in FIG. 2a, the sensor 14 includes a sensor reservoir 18 that encloses a sample volume 54 within four sides 56 (with only two sides 56 being shown) and a base 58. A detection system 60 is disposed in the reservoir 18, and includes a receptor layer 28 composed of antibodies to the protein to be detected, or is designed as an antibody layer on a seFET.

In addition, the sensor 14 includes a reservoir cap 16 atop the reservoir 18, with the cap 16 being disposed on or defining a sixth side 62 of the reservoir 18. The cap 16 closes the sample volume 54, at least in the closed state thereof, whereby neither the feature (analyte) 12 nor the receptor 60 can enter into or emerge from the sample volume 54. This is the preferred state of the sensor system 10 before a first measurement is performed, and between subsequent measurements. The cap 16 is designed as a controllable organic membrane 20 that can be reversibly changed between an open state and a closed state. For this purpose, the controllable organic membrane 20 includes pores 22 which are distributed homogeneously over the surface and have a diameter 24 that is reversibly changeable. For clarity, only a few pores 22 are shown in FIG. 1. In addition, the pores 22 are not shown with true dimensions/proportions, but rather are shown enlarged to better illustrate the operation of the sensor system 10.

Figure 3A:
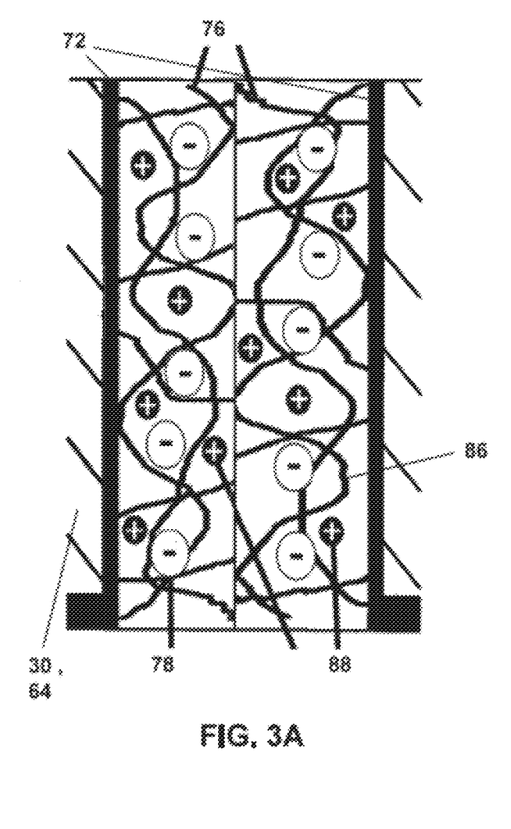
Figure 3B:
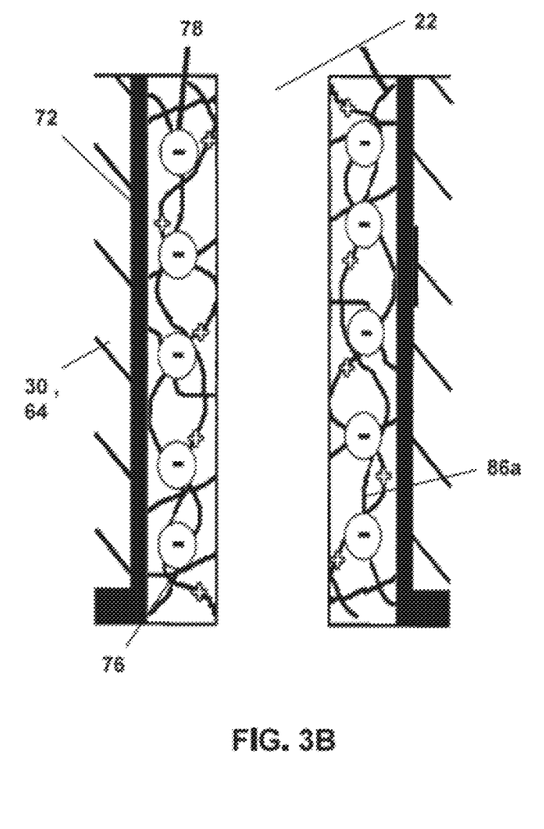

Moreover, the cap 16 includes a carrier structure 30 for the controllable organic membrane 20, which is formed by a nanoporous substrate of $TiO_2$ and therefore has high biocompatibility. The carrier structure 30 is formed by nanotubes 64 which extend perpendicularly to the base 58 of the reservoir 18, and parallel to each other. Each nanotube 64 has a nanopore 66 which is permeable for the analyte 50. The size of the nanopores 66 is determined by the feature 12 to be detected; for example, to measure cystatin C, a diameter of approximately 10 nm is preferred, and to measure glucose, a diameter of approximately 1 nm is preferred. The inner surface 68 of each nanopore 66 is coated, on a side 70 facing the base 58 (see FIG. 2a), with a conductive material 72 (e.g., with gold using a sputtering process). The controllable organic membrane 20 is disposed on the surface facing the sample volume 54. The controllable organic membrane 20 is electropolymerized from a solution of its components on the gold surface of the nanopores 66. The controllable organic membrane 20 is preferably formed by an electroactive polymer or material 74 that includes polypyrrole (PPy) 76 and dodecylbenzene sulfonic acid (DBS) 78 (see FIG. 3). To control the controllable organic membrane 20, printed conductor tracks 80 are installed on the carrier structure 30 at the level of the gold coating, and are connected to a control unit 82 integrated in the sensor 14, thereby enabling the controllable organic membrane 20 to be electrically controlled.

When manufacturing the carrier structure 30 or the nanotubes 64, the pore diameter can be easily adjusted, thereby making it possible to provide a large number of different carrier structures 30 which form the basic frameworks for the controllable organic membrane 20, in a manner tailored to analyte 50 to be used. A discussion of carrier/nanotube construction can be found, for example, in Albu et al., "Self-organized, free-standing TiO2 nanotube membrane for flow-through photocatalytic applications," Nano Lett. 2007 May; 7(5):1286-9 (Epub 2007 Apr. 25). Both this reference and Bauer et al., "TiO2 nanotubes: Tailoring the geometry in H3PO4/HF electrolytes," Electrochem. Commun 2006, 8, 1321-1325 (which is cited in Albu et al) discuss how the geometry of the nanotubes can be tailored during the formation process. The layer thickness of the membrane 20 is much greater (e.g. several 100 μm) than a diameter of nanotubes 64.

Due to the electroactive polymer 74, the controllable organic membrane 20 includes a material 26 that has a changeable redox state. As a result, it is possible to change or control the redox states via contacts between the conductive material 72 and the control unit 82 (which includes a reference electrode 84), and therefore change or control the volume of the electroactive polymer 74 or the controllable organic membrane 20. An increase in volume causes the nanopores 66 of the carrier structure 30 and the pores 22 of the controllable organic membrane 20 to close completely; conversely, a reduction in volume causes the nanopores 66 and the pores 22 for analyte 50 to open. Since the reduction of oxidation of the electroactive polymer 74 can take place to a partial extent, the opening of the nanopores 66 and the pores 22 can also be regulated partially and steplessly (continuously), thereby making it possible to target different analytes 50.

The sensor 14, the controllable organic membrane 20, and the carrier structure 30 are connected to the housing 52 in such a manner that substance can be exchanged only via the pore membrane and not via binding sites of the components.

FIGS. 3a and 3b show a pore 22 in a closed state (FIG. 3a) and in an open state (FIG. 3b). The electroactive polymer 74 is composed of a matrix 86 of cross-linked, positively charged fibers of polypyrrole 76. During polymerization, when the gold layer is being applied, negatively charged dodecylbenzene sulfonic acid (DBS) molecules 78 are inserted into the matrix 86 and, due to their size, are unable to diffuse out of the matrix 86, and represent the negatively charged counterions to the positively charged matrix 86 of the polypyrrole 76. When the polypyrrole 76 is fully reduced, it becomes electrically neutral.

The pores 22 are closed in the following manner. To compensate for the negative charge of the DBS molecules 78, positively charged, hydrated sodium ions 88 are inserted into the matrix 86a by applying a voltage (e.g., 2 volts). There, they result in a significant (up to 30%) lateral change in volume of the electroactive polymer 74. This change in volume causes the pores 22 to close and prevents structures from entering the sample volume 54. The process is reversed by applying a voltage having the opposite polarity, which then results in a reduction of the volume of the polymer 74. The reversibility of this procedure makes it possible to repeatedly open and close the pores 22. Furthermore, the volume of the controllable organic membrane 20 can be changed only partially via the extent of the reduction in the volume of the polymer 74. The particular redox states of the electroactive polymer 74 are created using different applied voltages, and can be retained by switching off the applied voltage.

The sensor system 10 can also be used to perform a quantitative determination of a concentration of the feature 12 of the analyte 50, as shown in FIGS. 2b and 2c. Region 32 defines both a first and a second sensor 14. To detect the feature 12, a first diameter 42 of the pores 22 of the controllable organic membrane 20 is adjusted in a first step and, in a second step, a second diameter 44 of the pores 22 is adjusted, with the first diameter 42 being smaller than second diameter 44. In the first step, a reference measurement is taken with the goal of ascertaining as many interfering signals as possible. The first diameter 42 is adjusted specifically such that the feature 12 or the analyte 50 cannot enter sample volume 54, e.g., to approximately 5 nm. However, smaller molecules, which could hamper the determination of the analyte 50, are unable to enter. In the second step, an analyte measurement is taken. In this case, second diameter 44 is enlarged only to the extent needed for the analyte 50 to enter the sample volume 54 in order to be measured (e.g., to approximately 10 nm for the measurement of cystatin C, or to 1 nm for the measurement of glucose). This can take place by applying different voltages, e.g., 1 V for a reference measurement and 1.5 V for the analyte measurement. As an alternative, if a constant voltage is applied (e.g. 2 V), the diameter can be changed in dependence on the duration for which the voltage is applied. Typical values are 4 minutes for the reference measurement and 5 minutes for the analyte measurement. To obtain a final measured result of the concentration of the analyte 50, the result of the analyte measurement can be corrected by the result of the reference measurement.

Figure 4:
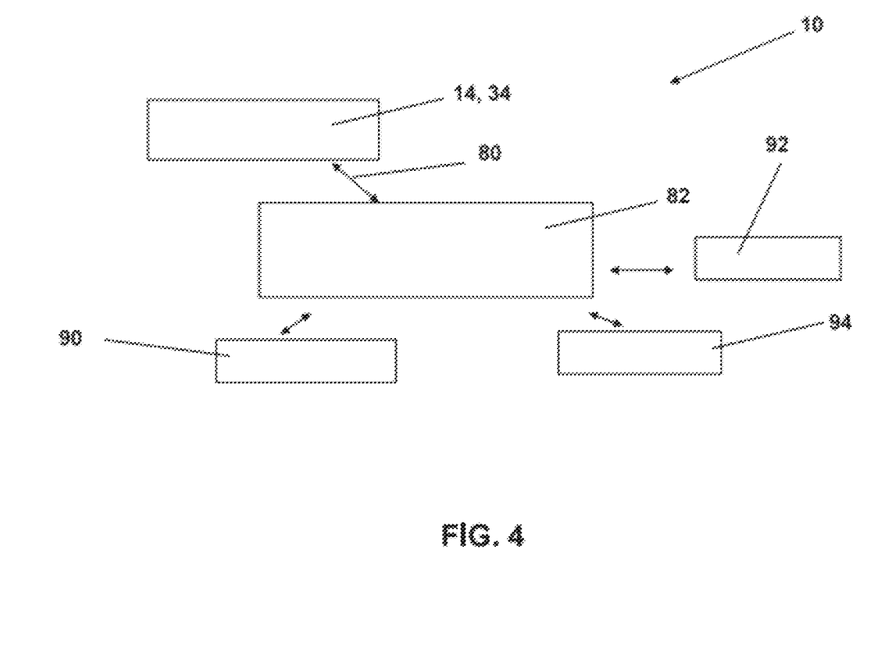

FIG. 4 shows a schematic illustration of the sensor system 10 with enhancements. In addition to the first (measurement) and second (reference) sensors 14, 34, the sensor system 10 includes a control unit 82 with printed conductor tracks 80 and further electronic components (not depicted), a program memory 90, a telemetry device 92, and a power supply 94. Using the telemetry device 92, the values detected by the sensor system 10 can be transmitted to an external device (not depicted). The telemetry device 92 is preferably designed for bidirectional communication, thereby enabling the sensor system 10 to be controlled by an external device. Furthermore, the sensor system 10 can communicate via the telemetry device 92 with further implanted devices, e.g. to control therapy or drug delivery by these further implanted devices, depending on the sensor values that are measured.

Figure 5A:
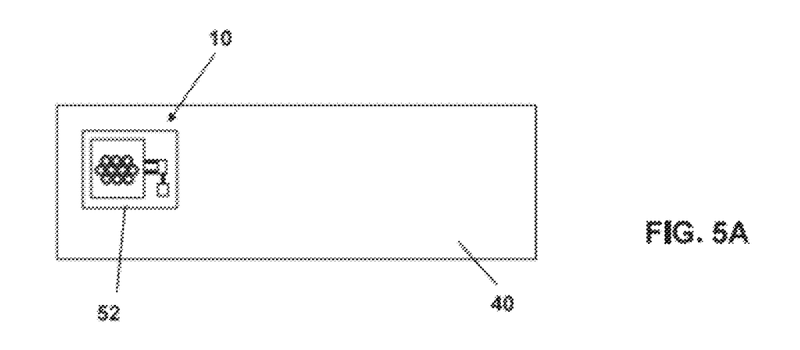
Figure 5B:
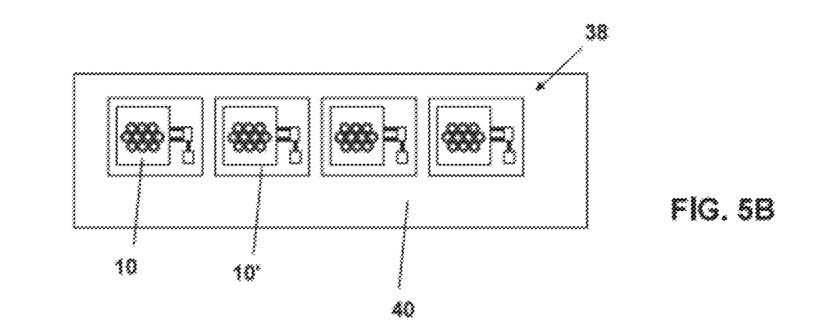

As shown in FIG. 5b, further sensor systems 10, 10' can be combined in a medical sensor array 38. In that case, a second sensor system 10' can be activated after the use of a first sensor system 10 or once the end of the service life of the first sensor system 10 has been reached.

FIGS. 5a and 5b illustrate the sensor system 10 (FIG. 5a) or the sensor array 38 (FIG. 5b) in a form suitable for implantation in a body by fastening it to a medical implant 40 using an anchoring device (not shown in detail). The implant 40 can be, for example, a memory-effect structure such as a stent, or a meandering structure for implantation in an artery or vein (not depicted). The anchoring device can be permanent or detachable.

Figure 6:
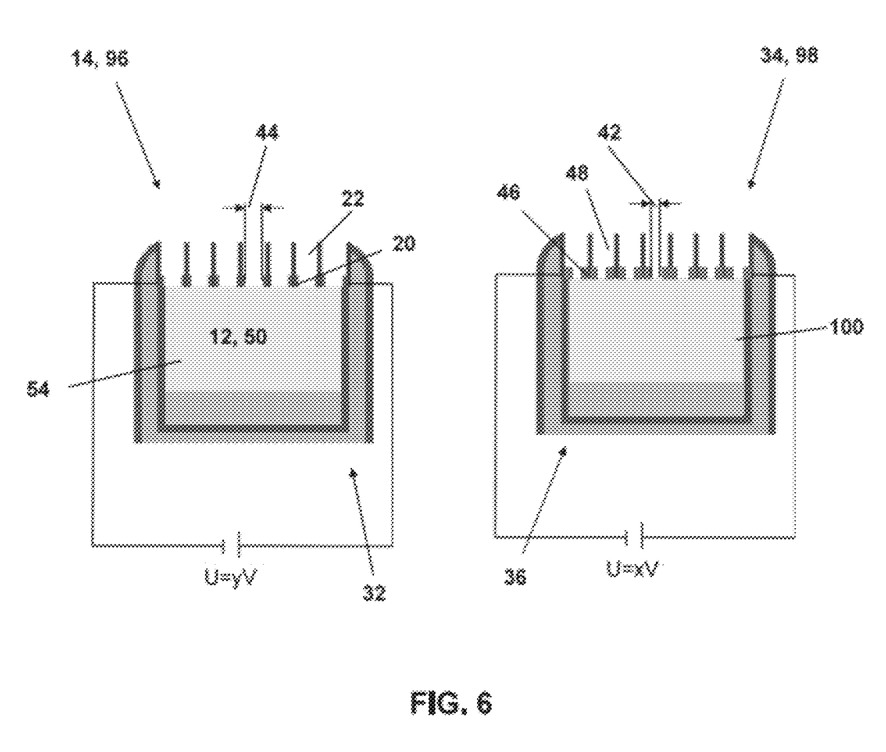
Figure 7A:
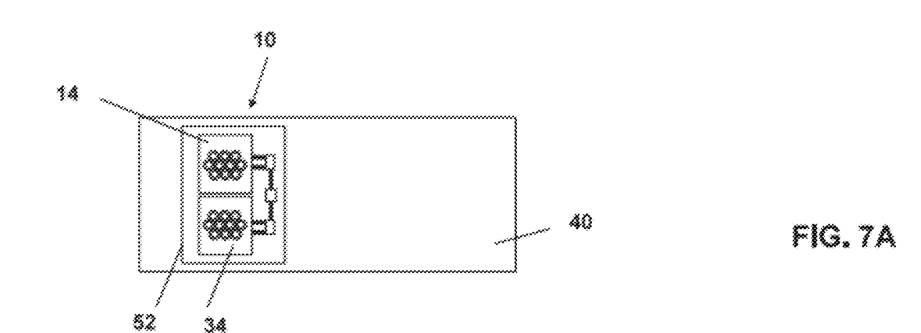
Figure 7B:
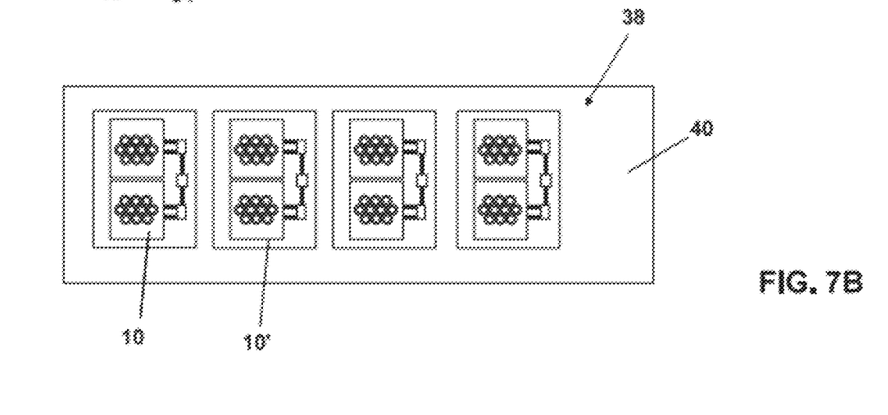

FIGS. 6, 7a and 7b show alternative versions of the sensor system 10, the sensor array 38, and the implant 40. Components, features, and functions that are essentially the same as those previously discussed are labeled using the same reference numerals. The description that follows is primarily limited to the differences from the version presented in FIGS. 1-5, and to the reader is directed to the description of the version shown in FIGS. 1-5 in regard to the components, features, and functions that remain the same.

FIG. 6 shows a cross section of an alternative medical sensor system 10 for detecting a feature 12 in a human or animal body, including a sensor 14 which includes a receptor layer 28 as its detection system 60. The sensor system 10 includes two different regions 32, 36 which are provided as a first sensor 14 and s second sensor 34. The sensors 14, 34 are disposed in a housing 52 such that they are spatially separated from each other (see FIG. 7a). The first sensor 14 is a measurement sensor 96, and the second sensor 34 is a reference sensor 98. Furthermore, each sensor 14, 34 includes a reservoir 18 which encloses a sample volume 54 or a reference volume 100. Each reservoir 18 is closed using a cap 16. Each cap 16 is designed as an electrically controllable organic membrane 20, 46 that contains an electroactive polymer 74 composed of polypyrrole and dodecylbenzene sulfonic acid (not shown in detail), thereby enabling the redox state of the material 28 of the polymers 74 to be changed.

The controllable organic membranes 20, 46 are each applied to a biocompatible carrier structure 30 composed of $TiO_2$. They also include the pores 22, 48, the diameter of which is reversibly changeable, thereby enabling the controllable organic membranes 20, 46 to be reversibly changed between an open state and a closed state of reservoir 18.

The reference sensor 98 is used to perform a reference measurement which can be used to obtain a background signal for correction of an analyte measurement of the sensor 14. For this purpose, in order to detect the feature 12, a first diameter 42 of the pore 48 of the controllable organic membrane 46 is adjusted on the controllable organic membrane 46 of the second sensor 34 (the reference sensor 98), and a second diameter 44 of the pore 22 of the controllable organic membrane 20 is adjusted on the controllable organic membrane 20 of the first sensor 14 (the measurement sensor 96), wherein the first diameter 42 is smaller than the second diameter 44. The first diameter 42 is specifically adjusted such that the feature 12 or the analyte 50 cannot enter the reference volume 100 of the sensor 34, e.g. approximately 5 nm when cystatin C is measured, and is less than 1 nm when glucose is measured. Smaller molecules, which could hamper the determination of the analyte 50, are unable to enter, however. The second diameter 44 of the pores 22 of the controllable organic membrane 20 of the first sensor 14 (the measurement sensor 96) is enlarged only to the extent that the analyte 50 can enter the sample volume 54 in order to be determined, e.g. to approximately 10 nm for the measurement of cystatin C or to approximately 1 nm for the measurement of glucose. The design of the sensors 14, 34 during measurement therefore differs merely by the implemented diameter 42, 44 of the pores 22, 48 of the controllable organic membranes 20, 46. This can take place by applying different voltages of (for example) 1V to the controllable organic membrane 20 of the first sensor 14 (the measurement sensor 96), and 1.5 V to the controllable organic membrane 46 of the second sensor 34 (the reference sensor 98). As an alternative, if a constant voltage is applied (e.g. 2 V), the diameters can be changed by the duration for which the voltage is applied, e.g., 4 minutes for the controllable organic membrane 20 of the first sensor 14 (the measurement sensor 96), and 5 minutes for the controllable organic membrane 46 of the second sensor 34 (the reference sensor 98).

The sensors 14, 34, the controllable organic membranes 20, 46, and the carrier structure 30 are connected to the housing 52 in a manner such that substances can be exchanged only via the pore membranes and not via binding sites of the components.

It would also be possible to design the controllable organic membranes 20, 46 as a single membrane having two parts that can be controlled independently of each other.

Several sensor systems 10, 10' can be combined in a medical sensor array 38, as shown in FIG. 7b. In this case, a second sensor system 10' can be activated after one or more uses of the first sensor system 10, or once the end of the service life of the first sensor system 10 has been reached.

As implied by FIGS. 7a and 7b, the sensor system 10 (FIG. 7a) or the sensor array 38 (FIG. 7b) can be implanted in a body by fastening it to a medical implant 40 using an anchoring device (not shown in detail).

It will be apparent to those skilled in the art that numerous modifications and variations of the described examples and versions of the invention are possible in light of the foregoing discussion. The described examples and versions are presented for purposes of illustration only, and it is the intent to cover all such modifications and alternate versions that come within the scope of the claims below, or which are legally equivalent thereto.

What is claimed is:

1. A method for operating a medical sensor system having:
   A. a reservoir having a reservoir interior sample volume and a reservoir exterior,
   B. a sensor situated within the reservoir interior sample volume, and
   C. a reservoir cap separating the reservoir interior sample volume and the reservoir exterior, wherein the cap is defined by an organic membrane having pores therein, the pores having controllably adjustable pore sizes, the method including the steps of:
   a. applying a stimulus to the cap to change it from a closed state wherein the pores are closed, with the cap thereby separating the sample volume from the exterior of the reservoir, to an intermediate state wherein the pores are open to less than their maximum pore sizes, thereby exposing the sample volume to the exterior of the reservoir;
   b. obtaining a reference reading from the sensor when the cap is in the intermediate state;
   c. applying a stimulus to the cap to change it to a measurement state wherein the pores are open to a desired pore size greater than the pore size at the intermediate state;
   d. obtaining a measurement reading from the sensor when the cap is in the measurement state;
   e. adjusting the measurement reading in dependence on the reference reading.

2. The method of claim 1, wherein the medical sensor system's reservoir interior sample volume is bounded by:
   a. the cap;
   b. a reservoir base opposite the cap, whereupon the sensor is provided; and
   c. reservoir sides extending between the cap and the reservoir base.

3. The method of claim 2, wherein the medical sensor system is in combination with a medical implant, wherein the medical sensor is provided on a surface of the medical implant with:
   a. the reservoir base situated adjacent the surface of the medical implant, and
   b. the cap situated distant from the surface of the medical implant.

4. The method of claim 1, wherein the medical sensor system is in combination with one or more of the following implants:
   a. a drug delivery system,
   b. a stent,
   c. a pacemaker,
   d. a defibrillator,
   e. an artificial valve,
   whereupon the medical sensor system is located.

5. The method of claim 1 wherein the applied stimulus is electrical.

6. The method of claim 1, wherein the membrane is at least partially formed of a material having a changeable redox state.

7. The method of claim 1, wherein the membrane is a polymer configured to change its redox state upon the application of electricity.

8. The method of claim 7, wherein the polymer includes one or more of:
a. polypyrrole (PPy), and
b. dodecylbenzene sulfonic acid (DBS).

9. The method of claim 1, wherein the cap is further defined by a carrier structure having apertures of fixed size defined therein, with the organic membrane provided within the apertures.

10. The method of claim 9, wherein the organic membrane is configured to change its redox state upon the application of electricity.

11. The method of claim 9, wherein the carrier structure has titanium dioxide therein.

12. The method of claim 9, wherein the apertures are defined by nanotubes.

13. The method of claim 9, wherein the apertures have inner surfaces bearing a conductor thereon.

14. The method of claim 1, wherein the pores are defined within nanotubes.

15. A method for operating a medical sensor system having a first medical sensor and a second medical sensor in close proximity, each medical sensor including:
A. a reservoir having a reservoir interior sample volume and a reservoir exterior,
B. a sensor situated within the reservoir interior sample volume, and
C. a reservoir cap separating the reservoir interior sample volume and the reservoir exterior, wherein the cap is defined by an organic membrane having pores therein, the pores having controllably adjustable pore sizes,
the method including the steps of:
a. applying a stimulus to the cap of the first medical sensor to change it from a closed state wherein the pores are closed, with the cap thereby separating the sample volume from the exterior of the reservoir, to an intermediate state wherein its pores are open to less than their maximum pore sizes, thereby exposing the sample volume to the exterior of the reservoir;
b. obtaining a reference reading from the sensor of the first medical sensor when the cap of the first medical sensor is in the intermediate state;
c. applying a stimulus to the cap of the second medical sensor to change it from a closed state wherein the pores are closed, with the cap thereby separating the sample volume from the exterior of the reservoir, to a measurement state wherein its pores are open to a desired pore size greater than the pore size of the first medical sensor at the intermediate state, thereby exposing the sample volume to the exterior of the reservoir;
d. obtaining a measurement reading from the sensor of the second medical sensor when its cap is in the measurement state;
e. adjusting the measurement reading in dependence on the reference reading.

16. The method of claim 15 wherein the applied stimulus is electrical.

17. The method of claim 15 wherein each medical sensor's membrane is at least partially formed of a material having a changeable redox state.

18. The method of claim 15 wherein each medical sensor's membrane is a polymer configured to change its redox state upon the application of electricity.

19. The method of claim 15 wherein each medical sensor's membrane includes a carrier structure having apertures of fixed size defined therein, with the membrane's pores being situated within the apertures.

20. The method of claim 15, wherein the medical sensor system is in combination with one or more of the following implants:
a. a drug delivery system,
b. a stent,
c. a pacemaker,
d. a defibrillator,
e. an artificial valve,
whereupon the first and second medical sensor are located.

* * * * *